United States Patent
Ichitani et al.

(10) Patent No.: US 8,611,634 B2
(45) Date of Patent: Dec. 17, 2013

(54) BLOOD AGGREGATION ABILITY MEASURING APPARATUS

(75) Inventors: Shuji Ichitani, Hachioji (JP); Osamu Toyama, Kakogawa (JP)

(73) Assignee: Konica Minolta Opto, Inc. (JP)

( * ) Notice: Subject to any disclaimer, the term of this patent is extended or adjusted under 35 U.S.C. 154(b) by 185 days.

(21) Appl. No.: 12/989,760

(22) PCT Filed: Apr. 14, 2009

(86) PCT No.: PCT/JP2009/057501
§ 371 (c)(1),
(2), (4) Date: Oct. 26, 2010

(87) PCT Pub. No.: WO2009/133769
PCT Pub. Date: Nov. 5, 2009

(65) Prior Publication Data
US 2011/0038524 A1     Feb. 17, 2011

(30) Foreign Application Priority Data
Apr. 30, 2008  (JP) .................................. 2008-118034

(51) Int. Cl.
*G06K 9/00* (2006.01)
(52) U.S. Cl.
USPC ........................................................ 382/134
(58) Field of Classification Search
None
See application file for complete search history.

(56) References Cited

U.S. PATENT DOCUMENTS

| | | | |
|---|---|---|---|
| 4,404,683 A * | 9/1983 | Kobayashi et al. | 382/134 |
| 5,023,054 A | 6/1991 | Sato | |
| 5,656,501 A * | 8/1997 | Yedgar et al. | 436/63 |
| 5,741,213 A * | 4/1998 | Kouchi et al. | 600/310 |
| 2006/0160165 A1* | 7/2006 | Phillips et al. | 435/13 |
| 2007/0076190 A1 | 4/2007 | Nakaya | |

FOREIGN PATENT DOCUMENTS

| | | |
|---|---|---|
| CA | 2129886 A1 | 2/1995 |
| DE | 68918223 T2 | 2/1995 |
| EP | 0368241 A2 | 5/1990 |
| EP | 0638799 A1 | 2/1995 |
| IL | 106662 A | 10/1996 |
| JP | 2-130471 A | 5/1990 |
| JP | 7-181178 A | 7/1995 |
| JP | 2685544 B2 | 12/1997 |
| JP | 10-48120 A | 2/1998 |
| JP | 10-90163 A | 4/1998 |

(Continued)

OTHER PUBLICATIONS

International Search Report for International Application No. PCT/JP2009/057501 mailed Jun. 23, 2009 with English translation.

(Continued)

*Primary Examiner* — Stephen R Koziol
*Assistant Examiner* — Amandeep Saini
(74) *Attorney, Agent, or Firm* — Cantor Colburn LLP

(57) ABSTRACT

To quantify the aggregation ability of various types of blood cells respectively within a short period of time. An apparatus for achieving the above-described object, which includes: a TV camera for taking an image of blood flow; an image processing section for identifying the types of blood cells contained in a blood cell retention part, in which blood cells are retained, from a blood flow image taken by the TV camera; and an aggregation ability calculation device for calculating at least one of the area, cell count and position of blood cells of each type as the aggregation ability of blood.

16 Claims, 12 Drawing Sheets

(56) References Cited

FOREIGN PATENT DOCUMENTS

| | | |
|---|---|---|
| JP | 2001-264318 A | 9/2001 |
| JP | 2006-71475 A | 3/2006 |
| JP | 2006-145345 A | 6/2006 |
| JP | 2007-93356 A | 4/2007 |

OTHER PUBLICATIONS

Notice of Reasons for Rejection for Japanese Application No. 2010-510078; Date of Mailing: Jul. 23, 2013, with English Translation.

* cited by examiner

S21

S22

S23

S24

S25

S26

S27

RED BLOOD CELL    WHITE BLOOD CELL    BLOOD PLATELET

BLOOD AGGREGATION ABILITY MEASURING APPARATUS

CROSS REFERENCE TO RELATED APPLICATIONS

This is a U.S. National Stage Application of International Application No. PCT/JP2009/057501 filed on 14 Apr. 2009. Priority under 35 U.S.C. §119(a) and 35 U.S.C. §365(b) is claimed from Japanese Application No. 2008-118034 filed 30 Apr. 2008, the disclosure of which is also incorporated herein by reference.

FIELD OF THE INVENTION

The present invention relates to a blood aggregation ability measuring apparatus.

BACKGROUND OF THE INVENTION

With increasing interest in health in recent years, particular importance has come to be given to the blood fluidity as a health barometer. The blood fluidity is commonly called the degree of smoothness of blood flow, which signifies that a smooth blood flow with high fluidity indicates good health. One of the ways of checking the blood fluidity disclosed so far is a technique for measuring the time required for blood to run through a filter having a microscopically small groove (see Patent Literature 1 for example).

Incidentally, the blood of lower fluidity tends to be subjected to aggregation where blood cell is retained to be combined into conglomerates. The methods for evaluating such a phenomenon include a technique by which the number and area of the retained white blood cell are calculated from the blood flow image where only the white blood cells have been selected by separation (see Patent Literature 2) and a technique by which the aggregation rate of the red blood cell is calculated from the blood flow image where only the red blood cells have been selected by separation (see Patent Literature 3).

In the techniques described in the above-mentioned Patent Literatures 2 and 3, the blood is separated into only the white blood cell or red blood cell. Instead of such method of separating into specific blood cells, another proposed method determines the type of the blood cells from the blood flow image according to the brightness ratio and the dispersion thereof, whereby the number of the blood cells is calculated (see Patent Literatures 4 and 5).

EARLIER TECHNOLOGICAL LITERATURE

Patent Literature

Patent Literature 1: Japanese Registration Patent No. 2685544
Patent Literature 2: Japanese Unexamined Patent Application Publication No. 2001-264318
Patent Literature 3: Japanese Unexamined Patent Application Publication No. 2006-71475
Patent Literature 4: Japanese Unexamined Patent Application Publication No. Hei 10-48120
Patent Literature 5: Japanese Unexamined Patent Application Publication No. Hei 10-90163

SUMMARY OF THE INVENTION

Problems to be Solved by the Invention

However, the methods described in the above-mentioned Patent Literatures 2 and 3 permit only the aggregation ability (ease of aggregation) of specific types of blood cell to be quantified. Further, these conventional methods require much time in calculating the quantitative value due to separation of blood cell into these specific types of blood cell. Furthermore, the methods of Patent Literatures 4 and 5 do not determine the aggregated blood cells. These methods have been unable to quantify the aggregation ability or to determine the type of the aggregated blood cells.

In view of the problems described above, it is an object of the present invention to provide a blood aggregation ability measuring apparatus capable of quantifying the aggregation ability of various types of blood cells in a short period of time.

Means for Solving the Problems

To solve the above-mentioned problems, the embodiment of Structure 1 is a blood aggregation ability measuring apparatus for measuring an aggregation ability of blood flowing in a constant direction, which includes: an image-taking device for taking an image of a flow of the blood; a blood cell type identification device for identifying at least one type of blood cell contained in a blood cell retention part when a blood cell is retained, from the image of the blood flow taken by the image-taking device; and an aggregation ability calculation device for calculating at least one of an area, a number and a position of blood cells of the at least one type of blood cell contained in the blood cell retention part, from the image of the blood flow taken by the image-taking device, based on a result of identification by the blood cell type identification device.

The embodiment of Structure 2 is a blood aggregation ability measuring apparatus described in Structure 1 wherein the aggregation ability calculation device calculates ratio of an area occupied by the at least one type of blood cell relative to an area of the blood cell retention part, or calculates ratio of a number of the blood cells of the at least one type of blood cell relative to a number of blood cells of all types of blood cell included in the blood cell retention part.

The embodiment of Structure 3 is a blood aggregation ability measuring apparatus described in Structure 1, which includes an aggregation order determination device for determining an aggregation order of a type of the blood cell contained in the blood cell retention part, wherein the aggregation ability calculation device calculates at least a position of blood cells of each type of blood cell contained in the blood cell retention part at prescribed time intervals, and wherein the aggregation order determination device determines the aggregation order, based on chronological change of the aggregation ability, such that a type of blood cell retained earlier in the blood cell retention part is ranked as a higher order.

The embodiment of Structure 4 is a blood aggregation ability measuring apparatus described in Structure 1, which includes an aggregation order determination device for determining an aggregation order of a type of the blood cell contained in the blood cell retention part, wherein the aggregation ability calculation device calculates at least a position of blood cells of each type of blood cell contained in the blood cell retention part, and wherein the aggregation order determination device determines the aggregation order such that a type of blood cell located more upstream of the blood flow in the blood cell retention part is ranked as a higher order.

The embodiment of Structure 5 is a blood aggregation ability measuring apparatus described in Structure 1 or 2, which includes an aggregation order determination device for determining an aggregation order of a type of the blood cell contained in the blood cell retention part, wherein the aggregation ability calculation device calculates at least an area or a number of blood cells of each type of blood cell contained in the blood cell retention part at prescribed time intervals, and wherein the aggregation order determination device determines the aggregation order, based on chronological change of the aggregation ability, such that a type of blood cell retained earliest in the blood cell retention part is ranked as a higher order than a type of blood cell retained later.

Effects of the Invention

According to the embodiment of Structure 1, it is provided with: an image-taking device for taking an image of a flow of the blood; a blood cell type identification device for identifying at least one type of blood cell contained in a blood cell retention part; and an aggregation ability calculation device for calculating at least one of an area, a number and a position of blood cells of each of the at least one type of blood cell contained in the blood cell retention part, from the image of the blood flow taken by the image-taking device, based on a result of identification by the blood cell type identification device. This allows the aggregation ability of at least one blood cell type to be quantified, without separating into a specific blood cell. Thus, the aggregation of at least one blood cell type can be quantified in a short period of time.

According to the embodiment of Structure 2, it calculates ratio of an area occupied by the at least one type of blood cell relative to an area of the blood cell retention part, or calculates ratio of a number of the blood cells of the at least one type of blood cell relative to a number of blood cells of all types of blood cell included in the blood cell retention part. This ensures enhanced precision in quantification of the aggregation ability also when there is a difference in the size of blood cell types.

According to the embodiment of Structure 3, the aggregation ability calculation device calculates at least a position of blood cells of each type of blood cell contained in the blood cell retention part at prescribed time intervals, and the aggregation order determination device determines the aggregation order, based on chronological change of the aggregation ability, such that a type of blood cell retained earlier in the blood cell retention part is ranked as a higher order. This ensures easy order-ranking of the positions of each type of blood cells as the quantified aggregation ability, and easier determination of the blood cell type of higher abnormality level.

According to the embodiment of Structure 4, the aggregation ability calculation device calculates at least a position of blood cells of each type of blood cell contained in the blood cell retention part, and the aggregation order determination device determines the aggregation order such that a type of blood cell located more upstream of the blood flow in the blood cell retention part is ranked as a higher order. This ensures order-ranking of the positions of each type of blood cells as the quantified aggregation ability, and easier determination of the blood cell type of higher abnormality level.

According to the embodiment of Structure 5, the aggregation ability calculation device calculates at least an area or a number of blood cells of each type of blood cell contained in the blood cell retention part at prescribed time intervals, and the aggregation order determination device determines the aggregation order, based on chronological change of the aggregation ability, such that a type of blood cell retained earliest in the blood cell retention part is ranked as a higher order than a type of blood cell retained later. This ensures order-ranking of the quantified aggregation ability of each blood cell type, and easier determination of the blood cell type of higher abnormality level.

BRIEF DESCRIPTION OF THE DRAWINGS

FIG. 8b is a chart showing the percentages of areas occupied by the red blood cell and blood platelet in FIG. 8a.

DESCRIPTION OF THE PREFERRED EMBODIMENT

The following describes the embodiments of the present invention with reference to drawings.

Figure 1:
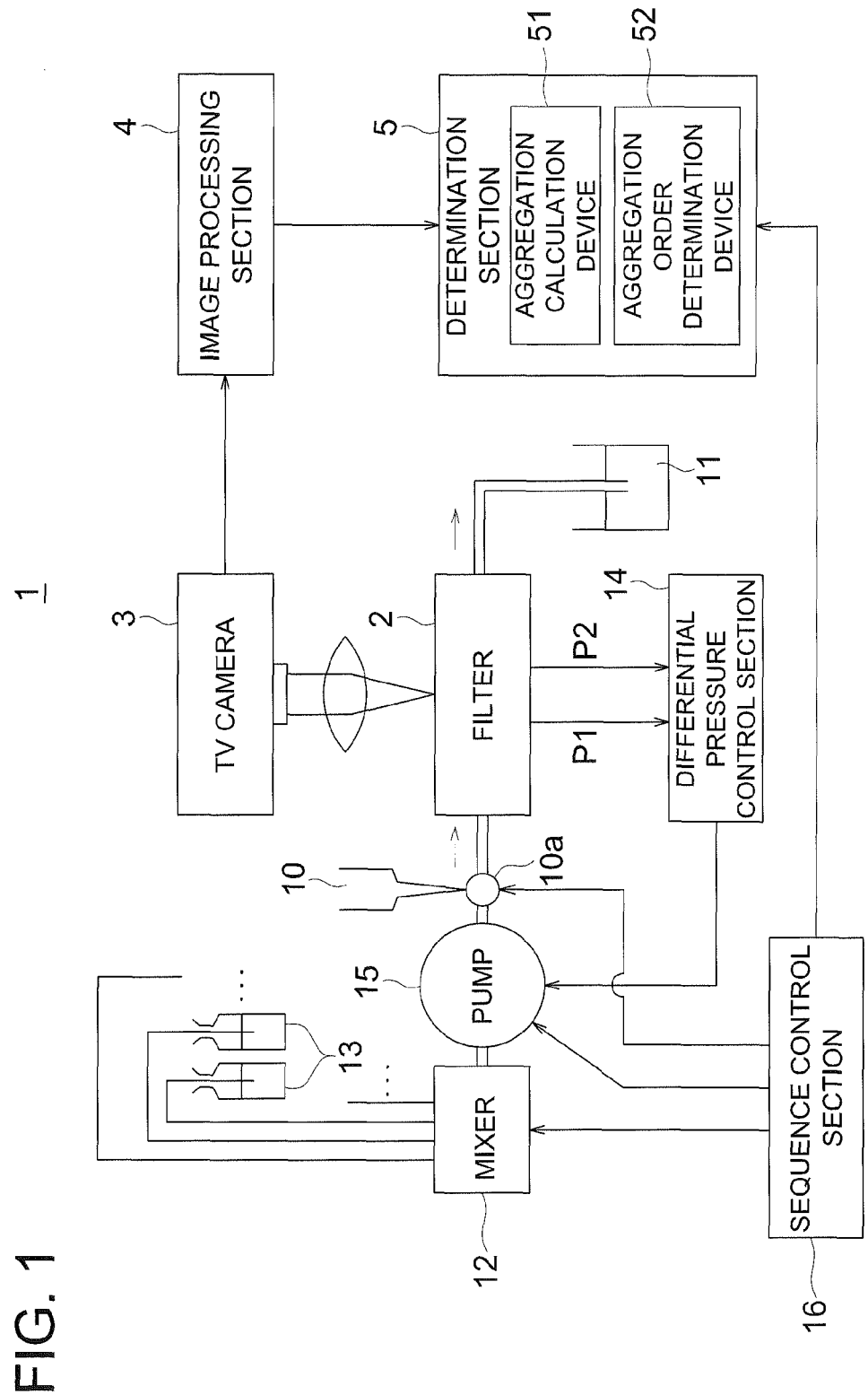
FIG. 1 is a block diagram showing the overall structure of a blood aggregation ability measuring apparatus.

FIG. 1 is a block diagram showing the overall structure of a blood aggregation ability measuring apparatus 1.

As shown in FIG. 1, the blood aggregation ability measuring apparatus 1 leads the blood supplied from an inlet 10 to be fed to the discharge tank 11 through a filter 2, and measures the aggregation ability of the blood based on the information obtained in this process. In this case, the aggregation ability indicates the quantitative value, to be described later, showing the degree of ease in the aggregation of blood. The aggregation indicates the conglomerate composed of the retained blood cell. The blood aggregation ability measuring apparatus 1 includes the major components of a filter 2, a TV camera 3 for taking an image of the flow of blood in the filter 2, an image processing section 4 for processing the blood flow image taken by the TV camera 3, and a determination section 5 for calculating the aggregation ability of each blood cell type of blood and determining the aggregation orders of the blood cell types.

The blood aggregation ability measuring apparatus 1 is provided with a plurality of solution bottles 13 which communicate with a flow path through a mixer 12 so that such a liquid as physiological saline solution or physiological active substance can be mixed with blood and led to the filter 2. When the differential pressure control section 14 controls a pump 15 to adjust the differential pressures before and after the filter 2, a desired amount of the blood mixed with such a liquid as physiological saline solution or physiological activated substance (hereinafter referred to as "blood") flows through the filter 2. Further, a mixer 12, pump 15, valve 10a of the inlet 10, and determination section 5 are integrally controlled by a sequence control section 16.

Figure 2:
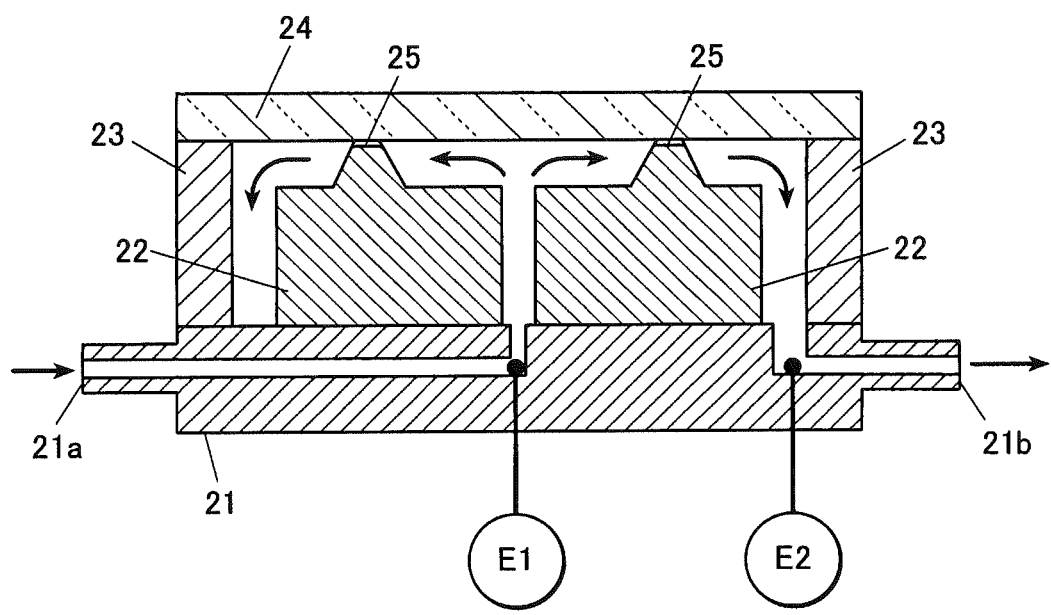
FIG. 2 is a side view in cross section of a filter.

As shown in FIG. 2, the filter 2 includes a base plate 21, a silicon single crystal substrate 22 fixed on the base plate 21, an outer plate 23 surrounding the side surface of the silicon single crystal substrate 22 and fixed on the base plate 21, and a glass flat plate 24 fixed on the outer plate 23. FIG. 2 is a side view in cross section of the filter 2. A hole section 25 composed of microscopic flow paths is formed between the silicon single crystal substrate 22 and glass flat plate 24. The base plate 21 is provided with an introduction port 21a communicating with the hole of the central portion of the silicon single crystal substrate 22, and a discharge port 21b communicating with the clearance between the silicon single crystal substrate 22 and outer plate 23. The introduction port 21a and discharge port 21b communicate with the inlet 10 and discharge tank 11 through tubes. This structure ensures that the blood led from the introduction port 21a into the filter 2 is discharged from the discharge port 21b through the hole section 25. The filter 2 is provided with pressure sensors E1 and E2 for measuring the pressure before and after the hole section 25. These pressure sensors E1 and E2 allow the measured pressure values P1 and P2 to be outputted to the differential pressure control section 14 (refer to FIG. 1).

Figure 3A:
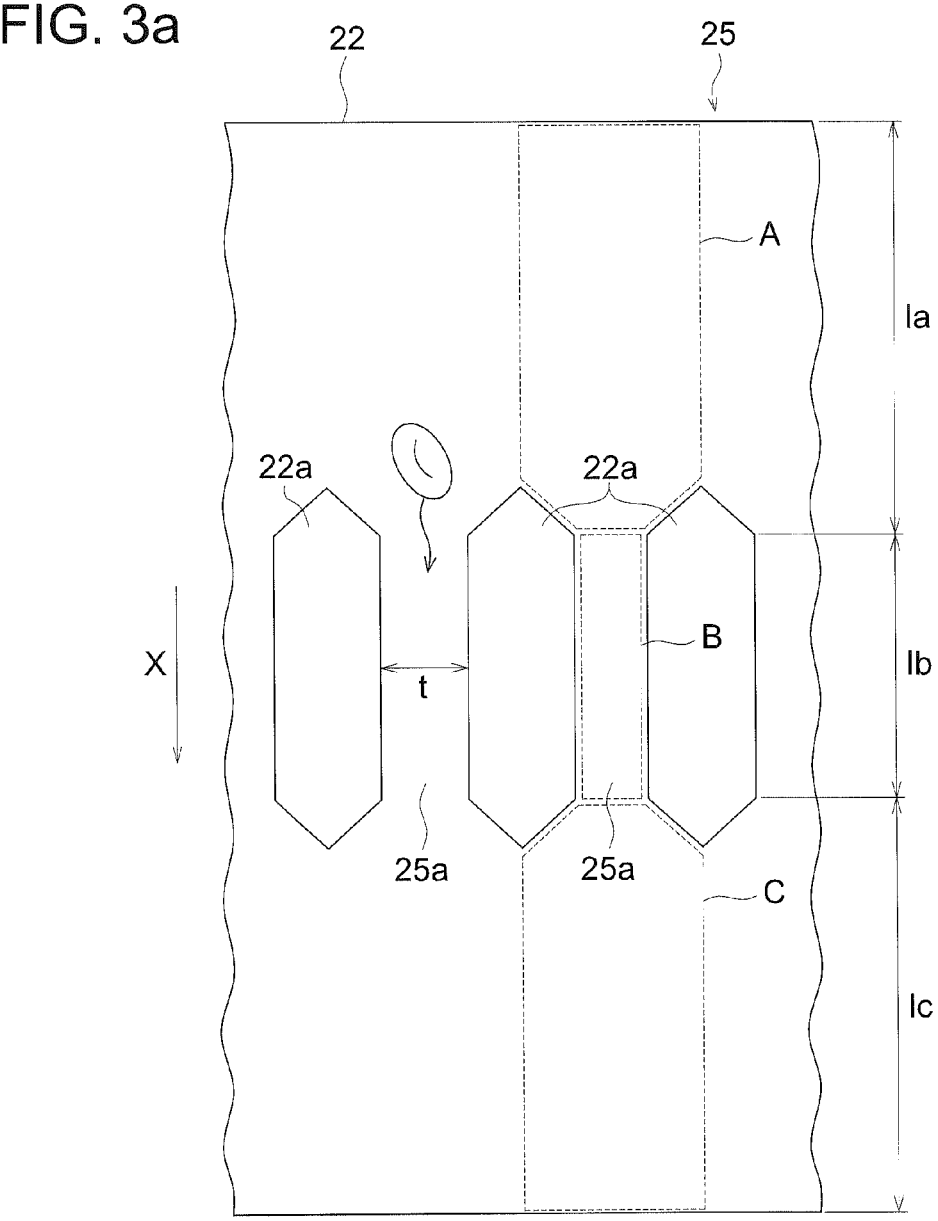
FIG. 3a is a partial top view of a hole.
Figure 3B:
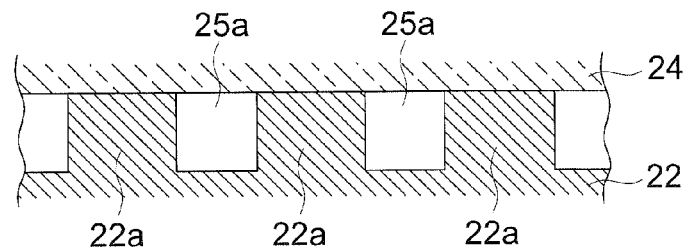
FIG. 3b is a side view in cross section thereof.

As shown in FIGS. 3a and 3b, the hole section 25 formed on the filter 2 includes a number of gates 25a formed as being sandwiched among a plurality of hexagonal bank portions 22a arranged on the silicon single crystal substrate 22. Here FIG. 3a is a partial top view of the hole section 25 as viewed from the side of the glass flat plate 24. FIG. 3b is a side view in cross section thereof. The bank portions 22a are formed on the central portion on the upper surface of the silicon single crystal substrate 22 along the width in the blood flow direction X, in such a way that the gates 25a are arranged in the direction perpendicular to the blood flow direction X. Although there is no particular restriction, the length 1a from the upstream end of the hole section 25 to the gate 25a, length 1b of the gate 25a, and length 1c from the gate 25a to the downstream end of the hole section 25 each are formed to be about 30 μm. The upper surfaces of these bank portions 22a are connected with the glass flat plate 24. The width "t" of the gate 25a is formed narrower than the diameter of the blood cell in the blood, for example, that of red blood cell R (about 8 μm). The blood cell in the blood, for example, the red blood cell R flowing through the hole section 25 formed in the above-mentioned way passes through the entrance area A upstream of the gate 25a. After that, the blood cell passes through the inner area B of the gate 25a by changing the shape, and then passes through the exit area C downstream of the gate 25a in the final stage.

The TV camera 3 is a digital CCD camera, for example, and is a high-speed camera having a sufficient resolution for capturing a blood flow image. As shown in FIG. 1, this TV camera 3 is installed above the filter 2. The image of the flow of the blood running through the hole section 25 is taken through a glass flat plate 24. The scope of image-taking includes the entrance area A, inner area B and exit area C in the plural gates 25a (FIG. 3). The blood flow image captured by the TV camera 3 is outputted to the image processing section 4 and is shown in a display which is not illustrated. The TV camera 3 is a camera capable of capturing a moving image, although there is no particular restriction thereto.

The image processing section 4 is equipped with an analysis device such as a CPU (Central Processing Unit) and a storage device (not illustrated) such as a semiconductor memory, and is electrically connected with the TV camera 3 and determination section 5. This image processing section 4 processes the blood flow image inputted from the TV camera 3, thereby identifying the type of the blood cell contained in the blood cell retention part of the blood flow, and outputting the same as image information to the determination section 5. The blood cell retention part in the sense which is used here, includes at least one retained blood cell. In the present invention, the blood cell type denotes any one of the red blood cell R, the white blood cell W and blood platelet T as the type of the blood cell. The blood cell indicates any solid component of the blood cell types. Determination of the blood cell type by the image processing section 4 should be conducted in at least one of the areas A through C of each gate 25a.

The determination section 5 is provided with an aggregation ability calculation device 51 for calculating the aggregation ability of various blood cell types and an aggregation order determination device 52 for determining the order of aggregation of the blood cell type, in addition to an analysis device such as a CPU (Central Processing Unit) and a storage device (not illustrated) such as a semiconductor memory. The determination section 5 is electrically connected with the image processing section 4. This determination section 5 calculates the aggregation ability of each blood cell type, based on the image information outputted from the image processing section 4, and assigns the order to the aggregation ability of blood cell type, thereby determining the aggregation order of the blood. The result of the calculated aggregation ability and the order of aggregation are indicated on a display which is not illustrated. Further, the determination section 5 is provided with various forms of data required to calculate the aggregation ability or to determine the order of aggregation. The determination section 5 and image processing section 4 can be arranged in one integral body using a PC or the like.

The aggregation ability calculation device 51 calculates the area, cell count and position of blood cells of each type contained in the blood cell retention part as the aggregation ability of the blood, based on the image information outputted from the image processing section 4. For the area, the aggregation ability calculation device 51 calculates the percentage of the area occupied by each of the blood cell types. For the cell count, the aggregation ability calculation device 51 also calculates the percentage in terms of the cell count of each of the blood cell types relative to all the blood cell types. The position in the sense which is used here refers to the coordinates within the horizontal surface of the hole section 25. Further, the aggregation ability calculation device 51 calculates the aggregation ability at prescribed time intervals. These time intervals can be set as desired. The aggregation ability calculation device 51 may be required only to calculate any one of the factors of the area, cell count and position of blood cells of each type contained in the blood cell retention part, without having to calculate all the above-mentioned items as aggregation ability. A configuration may be arranged such that the aggregation ability calculation device 51 calculates the above-mentioned items for at least one blood cell type, without having to calculate the above-mentioned items for all the blood cell types.

Based on the aggregation ability calculated by the aggregation ability calculation device 51, the aggregation order determination device 52 determines the aggregation order of the blood cell type contained in the blood cell retention part. The specific method of determining the order will be described later.

The following describes the operation of the blood aggregation ability measuring apparatus 1 when measuring the aggregation ability of the blood. It should be noted that measurement of the aggregation ability mentioned here includes not only the step of calculating the quantitative value as the aggregation ability, but also the step of determining the aggregation order of the blood cell types.

Figure 4:
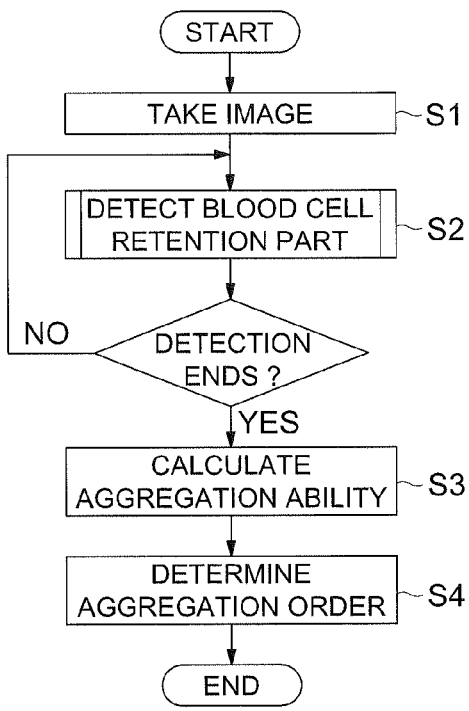
FIG. 4 is a flow diagram showing an aggregation ability measurement
Figure 5:
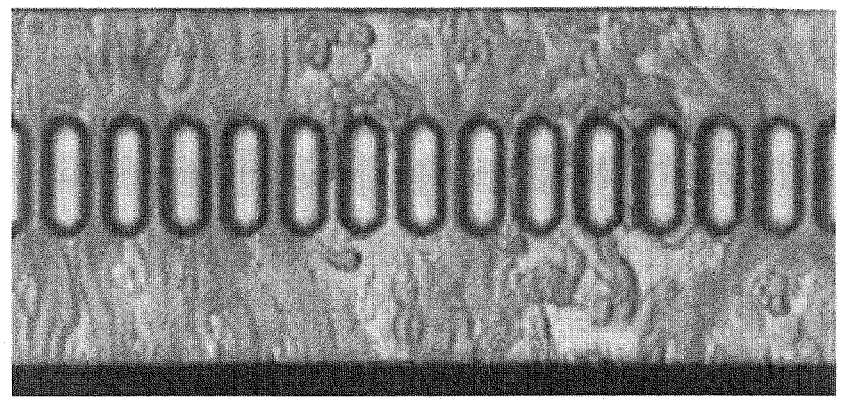
FIG. 5 is a diagram showing an example of a blood flow image.

As shown in FIG. 4, the image of the blood in the hole section 25 is taken (Step S1). FIG. 4 is a flow diagram showing an aggregation ability measurement. In this step, the blood to be measured is fed to the inlet 10 in the first place, and physiological saline solution is supplied to the solution bottle 13, as required. Then a prescribed differential pressure is applied to the filter 2 so that blood is supplied to the filter 2. At the same time, the moving images of the blood flow in the hole section 25 are captured by the TV camera 3. Thus, blood flow images are obtained by this image-taking, as shown in FIG. 5.

Figure 6:
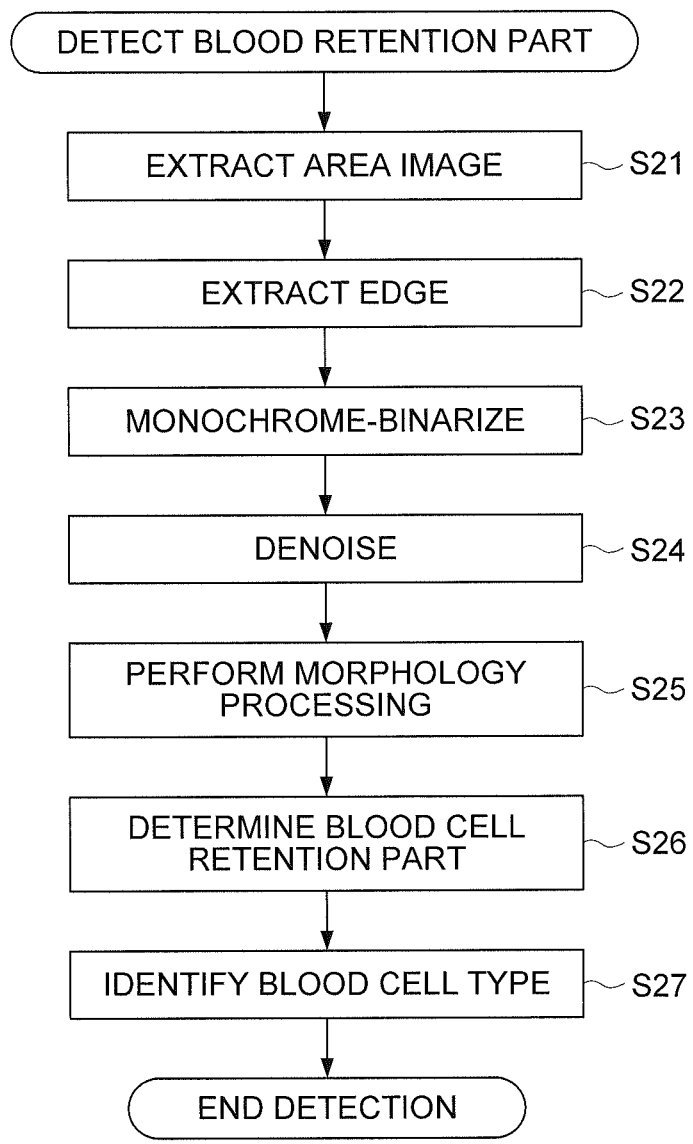
FIG. 6 is a flow diagram showing the detection of a blood cell retention part.

The blood flow image is processed by the image processing section 4, and the blood cell retention part in the blood flow is detected (Step S2). This step is carried out through the steps of FIG. 6 and processed images of FIGS. 7a through 7g. In this case, FIG. 6 is a flow diagram showing the detection of a blood cell retention part. FIGS. 7a through 7g show examples of the processed images in the exit area C in each of the steps for blood cell retention part detection.

In this case, the images of the entire area in any one of the areas A through C to be processed are extracted from all the blood flow images in the first place (Step S21). In the following description, it is assumed that the images of all the outlet areas C have been extracted.

The extracted image is passed through a Sobel filter in the vertical and horizontal directions, whereby the edge of the blood cell retention part is extracted (Step S22). This image is subjected to gray scale processing and is binarized using a prescribed threshold value, so that the blood cell retention part is shown in white (Step S23).

After binarization, the noise incorrectly identified as the edge of the blood cell retention part and the shade of blood flow are removed from the white portion (Step S24). In this case, the white portion in the area smaller than the preset threshold value is regarded as noise. The white portion where the ratio of the length in the direction of blood flow X relative to the length in the direction perpendicular thereto lies outside a prescribed range is regarded as the shade of blood flow, and is blackened.

Figure 7A:
FIG. 7a is a diagram representing the processed image in an area image extraction step of a gate outlet area.
Figure 7B:
FIG. 7b is a diagram representing the processed image in an edge extraction step.
Figure 7C:
FIG. 7c is a diagram representing the processed image in a monochrome-binarizing step.
Figure 7D:
FIG. 7d is a diagram representing the processed image in the noise processing step.
Figure 7E:
FIG. 7e is a diagram representing the processed image in the morphology processing step.
Figure 7F:
FIG. 7f is a diagram representing the processed image in the blood cell retention part determination step.
Figure 7G:
FIG. 7g is a diagram representing the processed image in the blood cell type determination step.
Figure 7G:
Figure 7G:
Figure 7G:
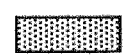

The image with the noise having been removed therefrom is subjected to processing of extension and contraction by the morphology processing. The clearances among the white portions are painted over (Step S25). The white portion remaining so far is determined as the blood cell retention part (Step S26). In FIG. 7f, different hatching is used for each of the white portions for ease of identification.

After the blood cell retention part has been determined, the blood cell type in the white portion is identified (Step S27). Hue is used to identify the red blood cell R. The white portion within the red hue range is determined as the red blood cell R. Brightness is used to identify the white blood cell W. Further, because of the greater size than that of other blood cell types, the white portion with smaller number of holes or the white portion having a smaller number of edges per unit area is determined as the white blood cell W. Brightness is used to identify the platelet T. In addition, because of the smaller size than that of other blood cell types, the white portion with a greater number of edges is determined as the platelet T.

In addition to the above-mentioned method of determination, the blood cell type can also be determined, for example, by using the methods disclosed in the Japanese Unexamined Patent Application Publication No. Hei 10-48120, Japanese Unexamined Patent Application Publication No. Hei 10-90163, and Japanese Unexamined Patent Application Publication No. Hei 10-275230.

After at least one blood cell type has been determined according to the above-mentioned methods, the position of the determined blood cell type is calculated by the following procedure. The first step is to extract the edges of the blood cell type having been determined in the blood cell retention part. Then, among these edges, the edge located on the most upstream side in the direction of blood flow X is determined to be the position of the blood cell type.

In the blood cell type determination step (S27), after the blood cell type contained in the blood cell retention part has been determined, the image information on the area, cell count and position of each of the blood cell types contained in the blood cell retention part is outputted from the image processing section 4 to the determination section 5. After that, the blood cell retention part detection Step S2 terminates.

Upon completion of the blood cell retention part detection Step S2, a step is taken to determine whether or not the blood cell retention part has been detected for all the blood flow images, as shown in FIG. 4. The blood cell retention part detection Step 2 is sequentially applied to the blood flow images where the blood cell retention part is not detected. All the blood flow images in the above description mean all the images having been extracted at prescribed time intervals from the moving image of the blood flow captured by the TV camera 3 in image-taking step S1.

Figure 8A:
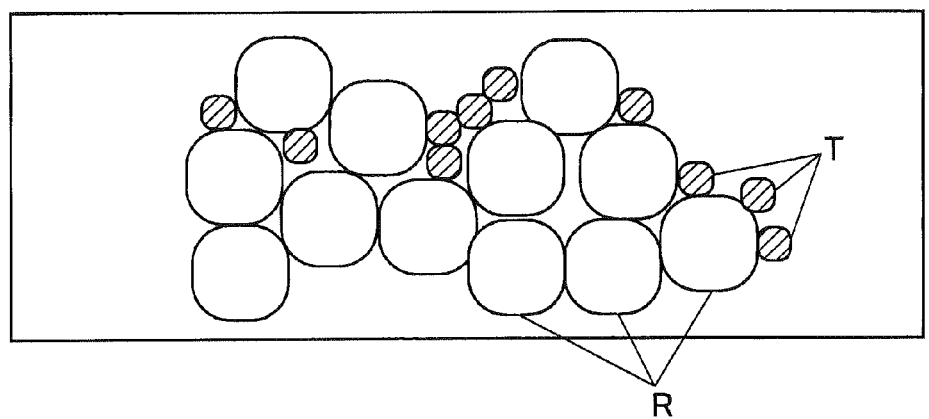
FIG. 8a is a diagram showing an example of the image information when a red blood cell and blood platelet are aggregated.
Figure 8B:
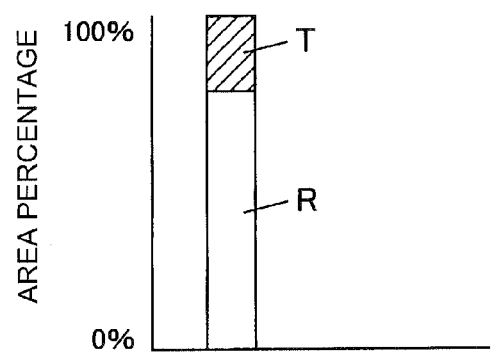

When the blood cell retention part in the blood flow has been detected for all the blood flow images, the aggregation ability of the blood is calculated by the aggregation ability calculation device 51 of the determination section 5 (Step S3). In this step, the aggregation ability is calculated based on the image information shown in FIG. 8a, for example, obtained in the blood cell retention part detection Step S2. In this case, FIG. 8a is a diagram showing an example of the image information where a red blood cell R and blood platelet T are aggregated. FIG. 8b is a chart showing the percentage of the areas occupied by the red blood cell R and platelet T. From the image information of FIG. 8a, the area, cell count or position of the red blood cells R and platelets T can be calculated as aggregation ability. Further, the percentage of the areas occupied by the red blood cell R and platelet T shown in FIG. 8b can be calculated from this image information, and can be used as the aggregation ability. Similarly, the percentage of cell count relative to the number of the blood cells of all the types can be obtained, and can be used as the aggregation ability. This arrangement improves precision in quantification of the aggregation ability when there are differences in the sizes of blood cell types. If these percentages of areas and cell count are used as the aggregation ability, the hematocrit value and blood cell count of the individual person can be used as denominators. This ensures aggregation ability to be calculated in a further standard manner. The above-mentioned hematocrit value and blood cell count of the individual person can be identified by blood examination. When the percentage of area is to be calculated as the aggregation ability, the area of the entire blood cell retention part can be used as a denominator, or the overall area of any one of the areas A through C where the blood cell retention part is present can be used as a denominator.

In the aggregation ability calculation step 3, the aggregation ability is calculated based on the information of all the blood flow images extracted at prescribed time intervals from the moving image of the blood flow. To put it another way, in the aggregation ability calculation step 3, the aggregation ability is calculated at prescribed time intervals.

Upon completion of the calculation of aggregation ability, the aggregation order of the blood cell type is determined by the aggregation order determination device 52 of the determination section 5, as shown in FIG. 4 (Step S4). In this step, the aggregation order of type of blood cells contained in the blood cell retention part is determined based on the aggregation ability calculated by the aggregation ability calculation device 51. At the same time, as this aggregation order is higher, the relevant blood cell type is ranked higher in the level of abnormality.

In the aggregation order determination Step S4, when the calculated aggregation ability is the area or cell count of each of the blood cell types, or the percentage of area or cell count, aggregation order is determined in such a way that the blood cell type having higher aggregation ability is ranked higher in the level of abnormality.

Figure 9A:
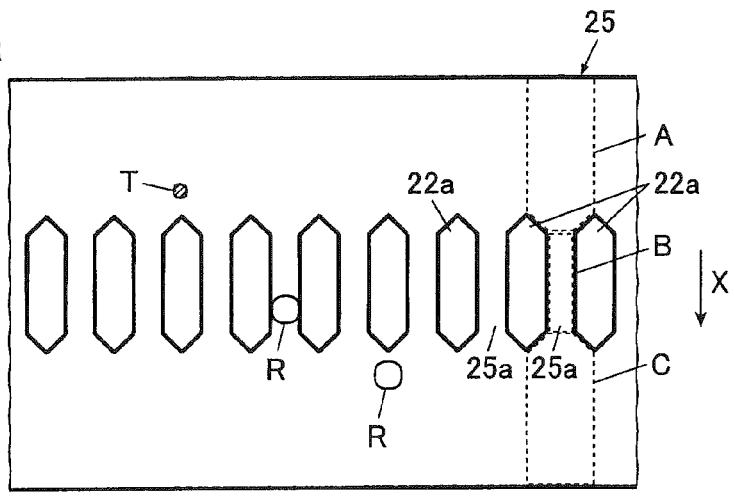
FIG. 9a is a diagram showing an example of the growth of the blood cell retention part in the hole.
Figure 9B:
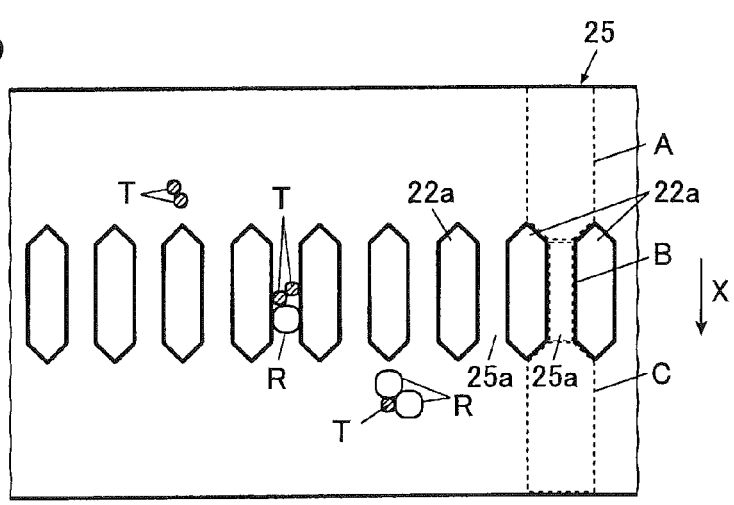
FIG. 9b is a diagram showing the growth of the blood cell retention part after the lapse of some time.
Figure 9C:
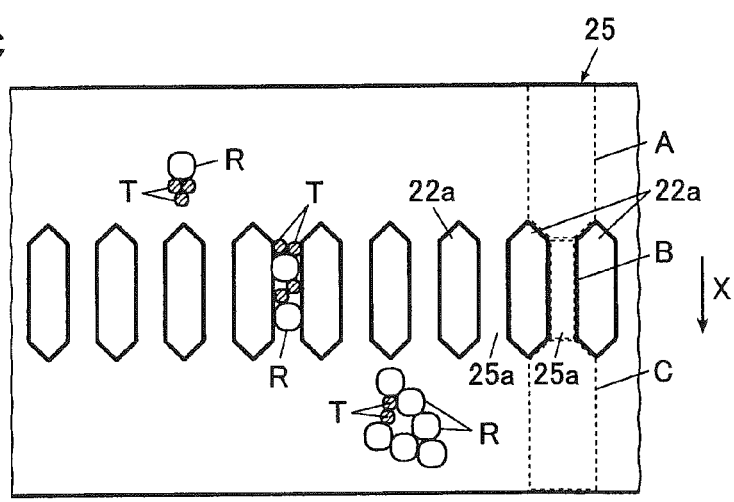
FIG. 9c is a diagram showing the state after a further lapse of time.

When the calculated aggregation ability is the position of each type of blood cells, the aggregation order is determined in such a way that the type of blood cell retained earlier in the blood cell retention part is ranked higher. In this case, if the chronological change of the position can be verified, the type of blood cell having been retained earlier is identified to ensure easy determination of the aggregation order. If not, that is, if only the position of each blood cell type at a particular time point can be calculated, determination is performed, taking advantages of the fact that the blood cell retention part grows in different directions, depending on the area where the blood cell retention part has occurred, as shown in FIGS. 9a through 9c. FIGS. 9a through 9c are diagrams showing the growth of the blood cell retention part in the hole section 25. Time is shown to have elapsed from FIG. 9a to FIG. 9c. As is apparent from these figures, the blood cell retention part occurring in the exit area C grows downstream in the direction of blood flow X with the lapse of time, and the blood cell retention part occurring in the inner area B or entrance area A grows upstream in the direction of blood flow X with the lapse of time. Thus, if the position of the blood cell retention part is found within the exit area C of the gate 25a, the blood cell type located upstream in the direction of blood flow X in the blood cell retention part is ranked higher. If the position of the blood cell retention part is found within the inner area B or entrance area A of the gate 25a, the blood cell type located downstream in the direction of blood flow X in the blood cell retention part is ranked higher. It should be noted that, when using the film without the gate 25a formed thereon, aggregation order should be determined in such a way that the blood cell type located upstream of the blood flow in the blood cell retention part is ranked higher.

When the calculated aggregation ability is related to any of the above-mentioned cases, the aggregation order is preferably determined by verifying the chronological changes. This is because chronological changes may be different even if the aggregation ability in a certain time is the same, as shown in FIGS. 10a through 10d and FIGS. 11a through 11d. FIGS. 10a through 10e are image information diagrams showing an example of the change in a blood cell retention part when time elapses in this order. FIG. 10d is a chart showing the chronological changes of the area percentage in the three diagrams. FIGS. 11a through 11c are image information diagrams showing another example of the change in a blood cell retention part when time elapses in this order. FIG. 11d is a chart showing the chronological changes of the area percentage in the three diagrams.

Figure 10A:
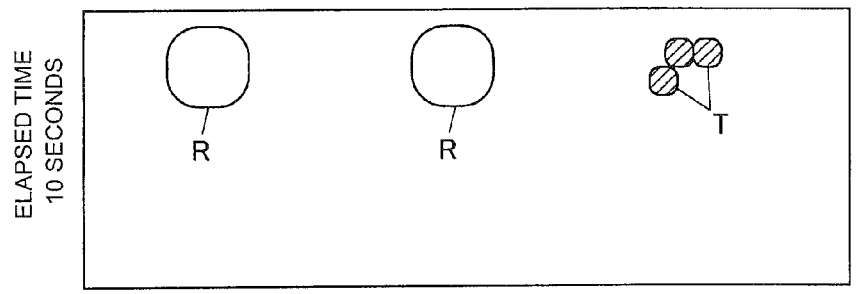
FIG. 10a is an image information diagram showing an example of the change in a blood cell retention part.
Figure 10B:
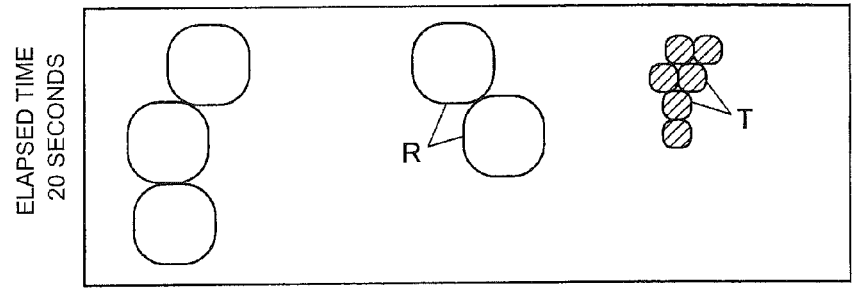
FIG. 10b is a diagram showing the state of the same drawing after the lapse of some time.
Figure 10C:
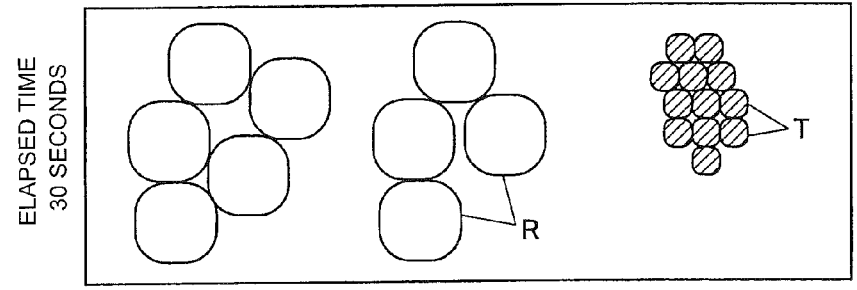
FIG. 10c is the state of the same drawing after a further lapse of time.
Figure 10D:
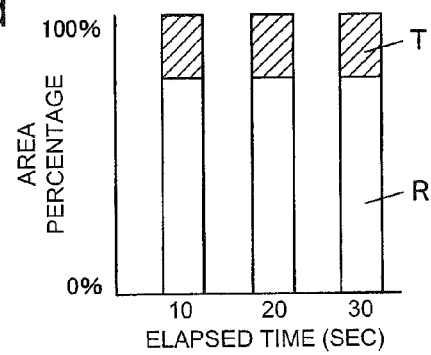
FIG. 10d is a chart showing the area percentage as aggregation ability in FIGS. 10a through 10c.
Figure 11A:
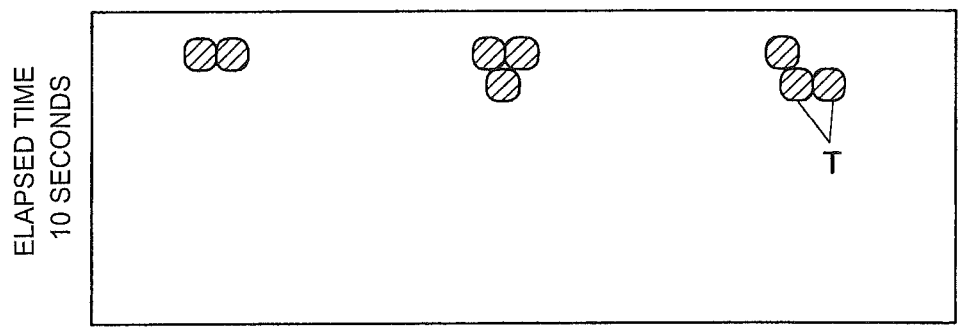
FIG. 11a is an image information diagram showing another example of the change in a blood cell retention part.
Figure 11B:
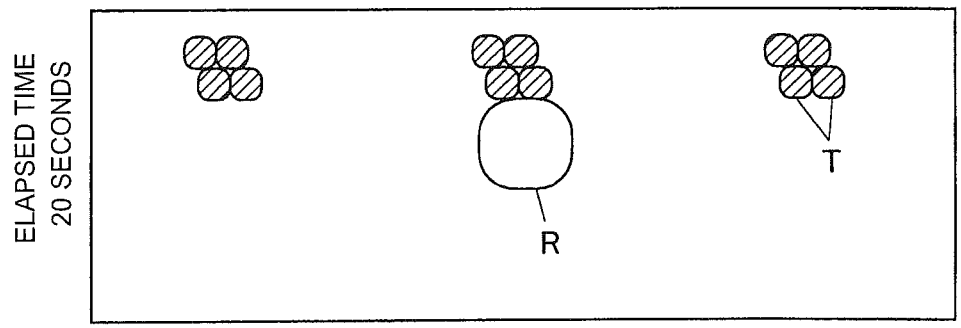
FIG. 11b is a diagram showing the state of the same drawing after the lapse of some time.
Figure 11C:
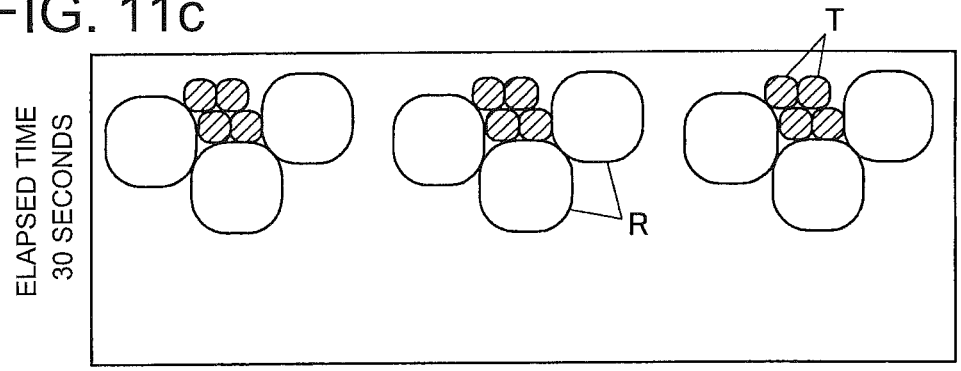
FIG. 11c is the state of the same drawing after a further lapse of time.
Figure 11D:
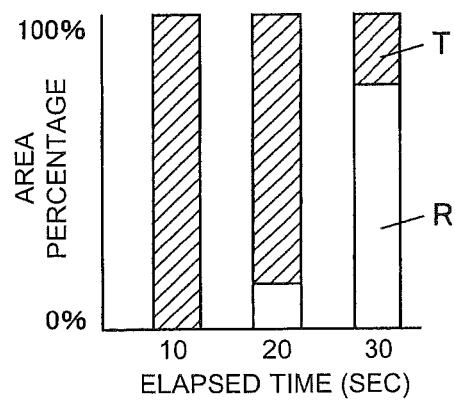
FIG. 11d is a chart showing the area percentage as aggregation ability in FIGS. 10a through 10c.

As shown in FIG. 10d and FIG. 11d, in the blood cell retention part of FIG. 10c and FIG. 11c showing the state after the lapse of 30 seconds, percentage of the areas of the red blood cell R and the platelet T is the same. However, going back in time, percentages of the areas of the red blood cell R and the platelet T are constant, independently of the lapse of time in FIG. 10d. In FIG. 11d, by contrast, the percentage of the area of the platelet T increases with the lapse of time. In this case, for the blood cell retention part of FIGS. 10a through 10d, the red blood cell R having a greater area percentage should be ranked higher. For the blood cell retention part of FIGS. 11a through 11d, the platelet T as the starting point should be ranked higher. As described above, even if the aggregation ability is the same at a certain time point, chronological changes may be different in some cases. Thus, aggregation order is preferably determined by verifying the chronological change.

Figure 12A:
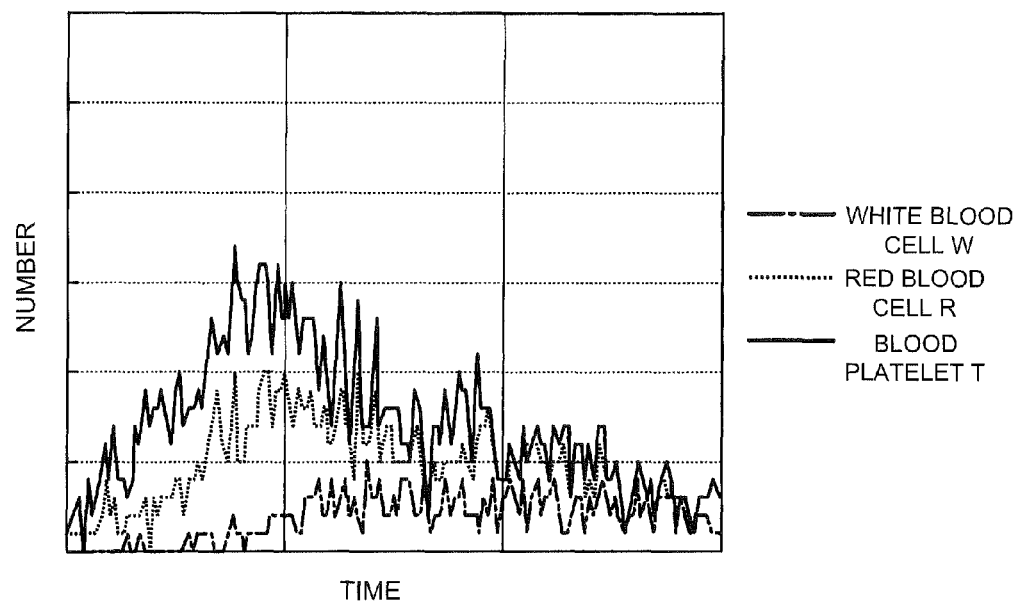
FIG. 12a is a chart showing an example of the chronological change in the number of blood cells of each blood cell type as aggregation ability.
Figure 12B:
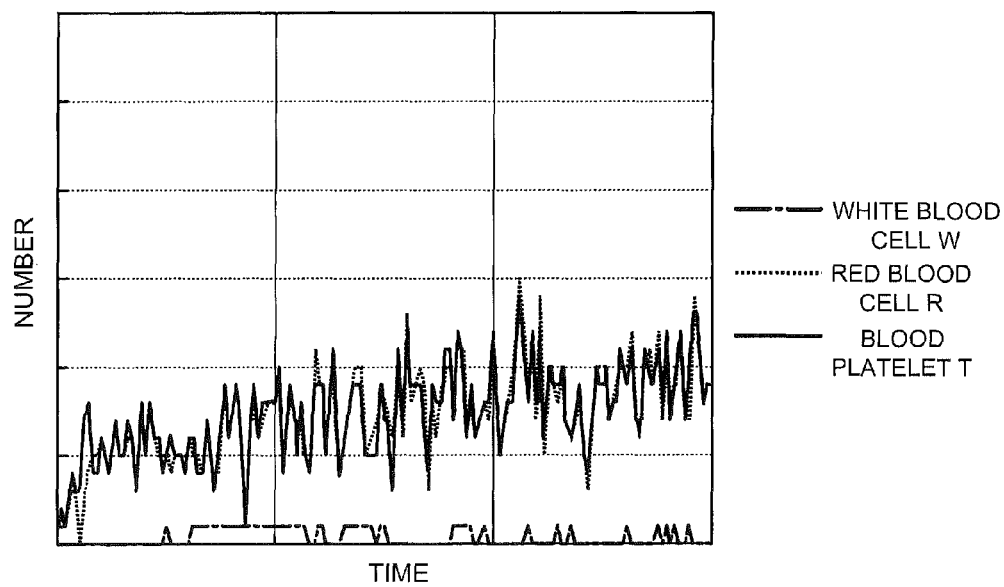
FIG. 12b is a chart showing another example.

As described above, if the chronological change of the aggregation ability can be verified, the aggregation order is determined in such a way that the type of blood cell having been retained earlier is ranked higher, by getting the chronological change of the aggregation ability, for example, from the aggregation ability calculation device 51, as shown in FIGS. 12a and 12b. FIG. 12a is a chart showing an example of the chronological change in the cell count of each blood cell type as aggregation ability, and FIG. 12b is a chart showing another example. In this case, in FIG. 12a, the platelet T is the first substance that forms the blood cell retention part, that is, the platelet T is retained earlier than any other substance. Thus, the platelet T is ranked the highest followed by the red blood cell R and white blood cell W in that order. Further, in FIG. 12b, the platelet T and red blood cell R are placed in the same rank, followed by the white blood cell W. It should be noted that, in this ranking, the aggregation ability can be any one of the area, area percentage and cell count percentage, without being restricted to the cell count.

For example, when the red blood cell R is ranked the highest by the determination of the aggregation order according to the chronological change of the aggregation ability, the red blood cell R is determined as abnormal. When the platelet T is ranked the highest, it goes without saying that the platelet T may be abnormal. However, for the blood of a patient with a lower possibility of having an abnormal platelet T, the platelet may have been activated by the impact at the time of blood collection. The determination of the aggregation order in such a case will provide reference data indicating that blood collection should be performed without giving impact to the patient.

If the chronological change of the aggregation ability can be verified, the level of abnormality of each blood cell type can be determined by checking the trend of the change. Referring to FIGS. 13a through 13d, the following describes the procedure of this determination. FIGS. 13a through 13d are diagrams showing different examples for the area of the red blood cell R as the aggregation ability subjected to chronological change.

Figure 13A:
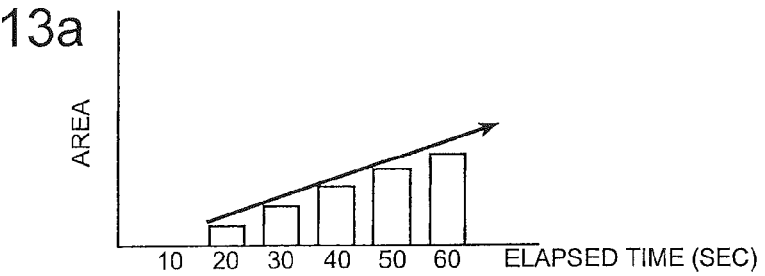
FIG. 13a is a diagram showing an example of the chronological change in the area of red blood cells as aggregation ability.
Figure 13B:
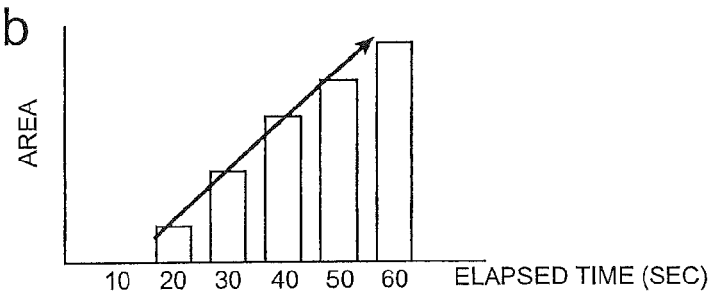
FIG. 13b is a diagram showing another example.
Figure 13C:
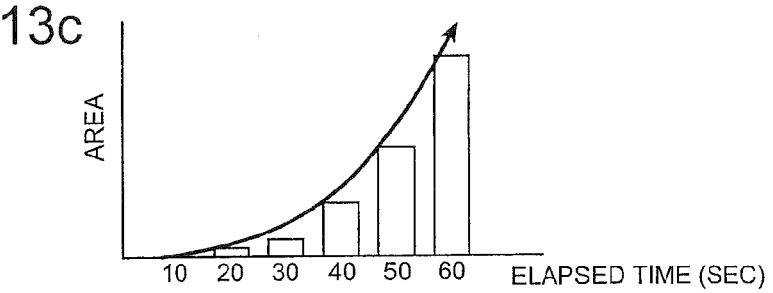
FIG. 13c is a diagram showing the second another example.

As shown in FIGS. 13a and 13b, when comparing two cases where there is a linear increase in area with the lapse of time, the inclination of the chronological change of this area is quantified. The red blood cell R of FIG. 13b characterized by greater inclination can be determined as higher in the level of abnormality. If a standard value is set as such an inclination, the standard level of abnormality can be determined by comparison with this value. Further, as shown in FIG. 13c, the red blood cell R exhibiting an accelerating increase with the lapse of time can be determined to be higher in the degree of abnormality than the red blood cell R whose area exhibits a linear increase, as shown in FIGS. 13a and 13b. When compared with the red blood cell R exhibiting the area of the similar characteristics, the red blood cell R having a greater range of increase can be determined to be higher in the level of abnormality. Such a method of determination is effective especially to the blood cell likely to aggregate such as the platelet T.

Figure 13D:
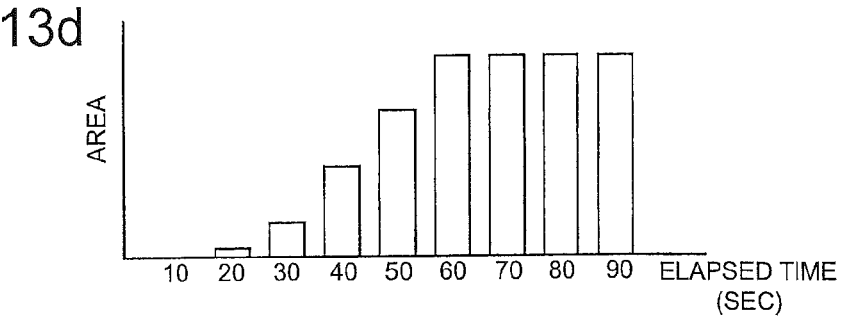
FIG. 13d is a diagram showing the third another example.

In some cases, a change stops after an increase to a certain level, as shown in FIG. 13d. In this case, when compared with the red blood cell R which has the similar tendency and whose inclination at the time of increase is on the same level, the red blood cell R which has a greater constant value is determined to have a higher level of abnormality. When compared with the red blood cell R which has the similar tendency and similar level of the constant value, the red blood cell R which has a greater inclination at the time of increase is determined to have a higher level of abnormality. Further, as shown in FIGS. 13a through 13c, when compared with the red blood cell R whose area continues to increase, the chronological change should be further verified, except when there is a marked difference between the two in the range of changing values. For example, when the level of abnormality is compared between the red blood cells R shown in FIGS. 13c and 13d, the chronological change of the area in FIG. 13c is further verified. As a result of this verification, if the area is increased further to exceed the constant value of the red blood cell R of FIG. 13d, the red blood cell R of FIG. 13c should be determined as higher in the level of abnormality. If the increase stops at a certain time point, it is preferred to use the above-mentioned method of comparing the red blood cells R having the similar tendency.

Figure 13E:
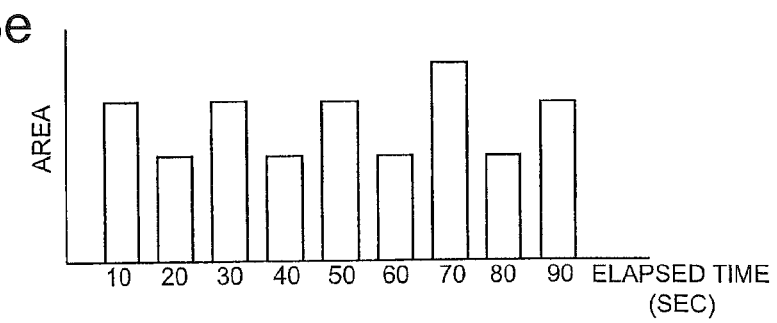
FIG. 13e is a diagram showing the fourth another example.

As shown in FIG. 13e, a certain tendency cannot be observed in the change of area in some cases. Such cases include the case where the red blood cell R repeats the process of aggregation and separation due to the abnormality of blood. In this case, the pattern of the area change caused by the abnormality of blood is set in advance. If agreement with this change pattern is verified, it is possible to determine whether or not the blood is abnormal or not. When determining each blood cell type according to the tendency in the change of the aggregation ability as described above, any one of the cell count, percentage of area and percentage of cell count can be used as the aggregation ability in place of area.

As described above, the blood aggregation ability measuring apparatus 1 of the present embodiment is provided with a TV camera 3 for taking an image of the flow of blood, an image processing section 4 for determining the blood cell type contained in the blood cell retention part, and an aggregation ability calculation device 51 for calculating at least one of the area, cell count and position of blood cells of each type contained in the blood cell retention part as the aggregation ability of blood. This structure permits the aggregation ability of each blood cell type to be quantified, without having to separate specific blood cells. This ensures the aggregation ability of each blood cell type to be quantified in a shorter period of time.

The aggregation ability calculation device 51 calculates at least the position of each type of blood cells contained in the blood cell retention part as aggregation ability, and the aggregation order determination device 52 determines the aggregation order of the type of blood cell contained in the blood cell retention part in such a way that the blood cell type located upstream in the direction of blood flow X in the blood cell retention part will be ranked higher. Thus, blood cell types where aggregation ability has been quantified are ranked in order, and the blood cell type in the higher level of abnormality is easily identified.

Further, the aggregation ability calculation device 51 calculates at least the area or cell count of blood cells of each type contained in the blood cell retention part as aggregation ability at prescribed time intervals. The aggregation order determination device 52 determines the aggregation order of the blood cell types contained in the blood cell retention part from the chronological change of the aggregation ability in such a way that the type of blood cell retained earlier in the blood cell retention part is ranked higher. Thus, the quantified aggregation ability of each of the blood cell types is ranked in order, and the blood cell type in the higher level of abnormality is easily identified.

The aggregation ability calculation device 51 calculates at least the position of each type of the blood cells contained in the blood cell retention part as aggregation ability at prescribed time intervals. The aggregation order determination device 52 determines the aggregation order of the type of the blood cells contained in the blood cell retention part from the chronological change of the aggregation ability in such a way that the type of blood cell retained earlier in the blood cell retention part is ranked higher. Thus, the position of each type of blood cells as the quantified aggregation ability is easily ranked in order, and the blood cell type in the higher level of abnormality is more easily identified.

In this embodiment, for ease of explanation of the blood cell retention part, only the red blood cell R and platelet T are used for explanation in most cases. It goes without saying that the white blood cell W can be included in the embodiment.

The hole section 25 of the filter 2 when the blood flows need not be provided with the gate 25a. It is only required that the blood flows in a substantially constant direction.

For other points, the present invention is not restricted to the above-mentioned embodiments. It goes without saying that the present invention can be embodied with appropriate modifications.

DESCRIPTION OF SYMBOLS

1. Blood aggregation ability measuring apparatus
3. TV camera (image-taking device)
4. Image processing section (blood cell type determination device)
51. Aggregation ability calculation device
52. Aggregation order determination device
X. Blood flow direction

What is claimed is:

1. A blood aggregation ability measuring apparatus for determining an order of an aggregation ability for each type of a plurality of types of blood cells in blood flowing in a constant direction, the blood aggregation ability measuring apparatus comprising:
    an image-taking device for taking an image of a flow of the blood;
    a blood cell type identification device for identifying blood cells of each type among the plurality of types of blood cells contained in a blood cell retention part where a blood cell is retained, from the image of the blood flow taken by the image-taking device;
    an aggregation ability calculation device for calculating at least one of an area, a number and positions of the blood cells of each type contained in the blood cell retention part, from the image of the blood flow taken by the image-taking device, based on a result of identification by the blood cell type identification device; and
    an aggregation order determination device configured to determine the order of the aggregation ability for the each type of the plurality of types of blood cells contained in the blood cell retention part based on chronological change related to the aggregation ability, calculated by the aggregation ability calculation device,
    wherein the image-taking device takes the image until any given elapsed time and the aggregation ability calculation device repeats the calculation of a plurality of blood cells in a prescribed calculation area at prescribed time intervals until the elapsed time and thereby calculates the chronological change related to the aggregation ability in the blood cell retention part, and
    wherein the prescribed calculation area is identical every time the calculation is repeated.

2. The blood aggregation ability measuring apparatus of claim 1,
    wherein the aggregation ability calculation device calculates ratio of an area occupied by the each type of the plurality of types of blood cells relative to an area of the blood cell retention part, or calculates ratio of a number of the blood cells of each type relative to a number of blood cells of all types of blood cell included in the blood cell retention part.

3. The blood aggregation ability measuring apparatus of claim 1,
    wherein the aggregation ability calculation device calculates at least a position of the blood cells of each type contained in the blood cell retention part at prescribed time intervals, and
    wherein the aggregation order determination device is configured to determine the order of the aggregation ability, by ranking a type of blood cell retained earlier in the blood cell retention part as a higher order.

4. The blood aggregation ability measuring apparatus of claim 1,
    wherein the aggregation ability calculation device calculates at least an area or a number of the blood cells of each type contained in the blood cell retention part at prescribed time intervals, and
    wherein the aggregation order determination device is configured to determine the order of aggregation ability, by ranking a type of blood cell retained earliest in the blood cell retention part as a higher order than a type of blood cell retained later.

5. The blood aggregation ability measuring apparatus of claim 1,
    wherein the plurality of blood cells in the prescribed calculation area are blood cells which are in contact with each other.

6. A blood aggregation ability measuring apparatus for determining an order of an aggregation ability for each type of a plurality of types of blood cells in blood flowing in a constant direction, the blood aggregation ability measuring apparatus comprising:
    an image-taking device for taking an image of a flow of the blood;
    a blood cell type identification device for identifying blood cells of each type among the plurality of types of blood cells contained in a blood cell retention part where a blood cell is retained, from the image of the blood flow taken by the image-taking device;
    an aggregation ability calculation device for calculating positions of the blood cells of each type contained in the blood cell retention part, from the image of the blood flow taken by the image-taking device, based on a result of identification by the blood cell type identification device; and
    an aggregation order determination device configured to determine the order of the aggregation ability for the each type of the plurality of types of the blood cells contained in the blood cell retention part by ranking a type of blood cell located more upstream of the blood flow in the blood cell retention part as a higher order based on the positions of the blood cells calculated by the aggregation ability calculation device.

7. The blood aggregation ability measuring apparatus of claim 6,
    wherein the aggregation ability calculation device calculates ratio of an area occupied by the each type of the plurality of types of blood cells relative to an area of the blood cell retention part, or calculates ratio of a number of the blood cells of each type relative to a number of blood cells of all types of blood cell included in the blood cell retention part.

8. The blood aggregation ability measuring apparatus of claim 6,
    wherein the blood cells in the blood cell retention part are blood cells which are in contact with each other.

9. A blood aggregation ability measuring method for determining an order of an aggregation ability for each type of a plurality of types of blood cells in blood flowing in a constant direction, the blood aggregation ability measuring method comprising:
    taking an image of a flow of the blood;
    identifying blood cells of each type among the plurality of types of blood cells contained in a blood cell retention part where a blood cell is retained, from the image of the blood flow taken in the image taking step;
    calculating at least one of an area, a number and positions of the blood cells of each type contained in the blood cell retention part, from the image of the blood flow taken in the image taking step, based on a result of identification in the identifying step; and
    determining the order of the aggregation ability for the each type of the plurality of types of blood cells contained in the blood cell retention part based on chronological change related to the aggregation ability, calculated in the calculating step,
    wherein the image is taken until any given elapsed time in the image taking step and the calculation of a plurality of blood cells in a prescribed calculation area is repeated at prescribed time intervals until the elapsed time and thereby the chronological change related to the aggregation ability in the blood cell retention part is calculated in the calculating step, and wherein the prescribed calculation area is identical every time the calculation is repeated.

10. The blood aggregation ability measuring method of claim 9, wherein, in the calculating step, ratio of an area occupied by the each type of the plurality types of blood cells relative to an area of the blood cell retention part is calculated or ratio of a number of the blood cells of each type relative to a number of blood cells of all types of blood cell included in the blood cell retention part is calculated.

11. The blood aggregation ability measuring method of claim 9, wherein, in the calculating step, at least a position of the blood cells of each type contained in the blood cell retention part is calculated at prescribed time intervals, and wherein, in the determining step, the order of the aggregation ability is determined by ranking a type of blood cell retained earlier in the blood cell retention part as a higher order.

12. The blood aggregation ability measuring method of claim 9, wherein, in the calculating step, at least an area or a number of the blood cells of each type contained in the blood cell retention part is calculated at prescribed time intervals, and wherein, in the determining step, the order of aggregation ability is determined by ranking a type of blood cell retained earliest in the blood cell retention part as a higher order than a type of blood cell retained later.

13. The blood aggregation ability measuring method of claim 9, wherein the plurality of blood cells in the prescribed calculation area are blood cells which are in contact with each other.

14. A blood aggregation ability measuring method for determining an order of an aggregation ability for each type of a plurality of types of blood cells in blood flowing in a constant direction, the blood aggregation ability measuring method comprising:

taking an image of a flow of the blood;

identifying blood cells of each type among the plurality of types of blood cells contained in a blood cell retention part where a blood cell is retained, from the image of the blood flow taken in the image taking step;

calculating positions of blood cells of each type contained in the blood cell retention part, from the image of the blood flow taken in the image taking step, based on a result of identification in the identifying step; and determining the order of the aggregation ability for each type of the plurality of types of the blood cells contained in the blood cell retention part by ranking a type of blood cell located more upstream of the blood flow in the blood cell retention part as a higher order based on the positions of the blood cells calculated in the calculating step.

15. The blood aggregation ability measuring method of claim 14, wherein, in the calculating step, ratio of an area occupied by the each type of the plurality of types of blood cells relative to an area of the blood cell retention part is calculated or ratio of a number of the blood cells of each type relative to a number of blood cells of all types of blood cell included in the blood cell retention part is calculated.

16. The blood aggregation ability measuring method of claim 14, wherein the blood cells in the blood cell retention part are blood cells which are in contact with each other.

* * * * *